United States Patent
Shigetou

(10) Patent No.: US 8,199,018 B2
(45) Date of Patent: Jun. 12, 2012

(54) DETECTOR FOR STATE OF PERSON

(75) Inventor: Kazuhide Shigetou, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 640 days.

(21) Appl. No.: 12/089,337

(22) PCT Filed: Oct. 26, 2006

(86) PCT No.: PCT/JP2006/321918
§ 371 (c)(1),
(2), (4) Date: Apr. 4, 2008

(87) PCT Pub. No.: WO2007/052729
PCT Pub. Date: May 10, 2007

(65) Prior Publication Data
US 2010/0076273 A1      Mar. 25, 2010

(30) Foreign Application Priority Data
Oct. 31, 2005   (JP) ................................. 2005-316773

(51) Int. Cl.
*G08B 23/00* (2006.01)
(52) U.S. Cl. ..................... 340/573.1; 340/575; 340/576; 600/300; 600/544
(58) Field of Classification Search .................. 600/300, 600/544; 340/575, 576, 573.1
See application file for complete search history.

(56) References Cited

U.S. PATENT DOCUMENTS

| | | | | |
|---|---|---|---|---|
| 3,087,487 A | * | 4/1963 | Clynes | 600/544 |
| 3,468,302 A | * | 9/1969 | Cowell | 600/547 |
| 3,513,834 A | * | 5/1970 | Suzuki et al. | 600/544 |
| 3,915,154 A | * | 10/1975 | Cosentino | 128/898 |
| 4,088,125 A | * | 5/1978 | Forgione et al. | 600/547 |

(Continued)

FOREIGN PATENT DOCUMENTS

JP       A-3-151938       6/1991

(Continued)

OTHER PUBLICATIONS

Nov. 11, 2009 Search Report issued in European Patent Application No. 06822838.6.

*Primary Examiner* — Benjamin C Lee
*Assistant Examiner* — Quang D Pham
(74) *Attorney, Agent, or Firm* — Oliff & Berridge, PLC

(57) ABSTRACT

An object of the present invention is to provide a human condition detecting apparatus for highly accurately detecting a human condition, without any burden. A human condition detecting apparatus of the present invention is characterized by comprising a first stimulus applying device 10 for applying a stimulus for acquisition of reference information to a subject; a second stimulus applying device 10 for applying a stimulus for acquisition of condition information to the subject; a stimulus reaction detecting device 20 for detecting reactions of the subject to the stimulus applied by the first stimulus applying device 10 and to the stimulus applied by the second stimulus applying device 10, by an ecological index of the subject; and a condition determining device 41 for determining a condition of the subject, based on a comparison between the reaction of the subject to the stimulus applied by the first stimulus applying device 10 and the reaction of the subject to the stimulus applied by the second stimulus applying device 10.

8 Claims, 9 Drawing Sheets

U.S. PATENT DOCUMENTS

| | | | | |
|---|---|---|---|---|
| 4,195,626 A * | 4/1980 | Schweizer | | 600/587 |
| 4,201,224 A * | 5/1980 | John | | 600/544 |
| 4,502,122 A * | 2/1985 | Yanagishima et al. | | 340/575 |
| 4,570,640 A * | 2/1986 | Barsa | | 600/554 |
| 4,706,072 A * | 11/1987 | Ikeyama | | 340/576 |
| 4,854,329 A * | 8/1989 | Walruff | | 600/558 |
| 4,869,264 A * | 9/1989 | Silberstein | | 600/544 |
| 4,883,067 A * | 11/1989 | Knispel et al. | | 600/545 |
| 4,928,090 A * | 5/1990 | Yoshimi et al. | | 340/575 |
| 5,127,708 A * | 7/1992 | Kishi et al. | | 297/284.1 |
| 5,219,322 A * | 6/1993 | Weathers | | 600/27 |
| 5,259,390 A * | 11/1993 | MacLean | | 600/552 |
| 5,311,877 A * | 5/1994 | Kishi | | 600/545 |
| 5,447,166 A * | 9/1995 | Gevins | | 600/544 |
| 5,453,929 A * | 9/1995 | Stove | | 701/1 |
| 5,474,081 A * | 12/1995 | Livingstone et al. | | 600/544 |
| 5,488,353 A * | 1/1996 | Kawakami et al. | | 340/576 |
| 5,573,006 A * | 11/1996 | Shimotani et al. | | 600/558 |
| 5,595,488 A * | 1/1997 | Gozlan et al. | | 434/236 |
| 5,642,093 A * | 6/1997 | Kinoshita et al. | | 340/439 |
| 5,689,241 A * | 11/1997 | Clarke et al. | | 340/575 |
| 5,745,031 A * | 4/1998 | Yamamoto | | 340/439 |
| 5,810,747 A * | 9/1998 | Brudny et al. | | 600/595 |
| 5,813,993 A * | 9/1998 | Kaplan et al. | | 600/544 |
| 5,815,070 A * | 9/1998 | Yoshikawa | | 340/439 |
| 5,888,074 A * | 3/1999 | Staplin et al. | | 434/258 |
| 5,906,208 A * | 5/1999 | Ishikawa et al. | | 128/898 |
| 5,917,415 A * | 6/1999 | Atlas | | 340/575 |
| 6,014,081 A * | 1/2000 | Kojima et al. | | 340/576 |
| 6,024,575 A * | 2/2000 | Ulrich | | 434/236 |
| 6,167,298 A * | 12/2000 | Levin | | 600/545 |
| 6,172,610 B1 * | 1/2001 | Prus | | 340/575 |
| 6,265,978 B1 * | 7/2001 | Atlas | | 340/575 |
| 6,275,723 B1 * | 8/2001 | Ferris et al. | | 600/417 |
| 6,304,187 B1 * | 10/2001 | Pirim | | 340/576 |
| 6,346,887 B1 * | 2/2002 | Van Orden et al. | | 340/575 |
| 6,353,396 B1 * | 3/2002 | Atlas | | 340/693.9 |
| 6,497,658 B2 * | 12/2002 | Roizen et al. | | 600/301 |
| 6,620,100 B2 * | 9/2003 | Smits et al. | | 600/300 |
| 6,623,427 B2 * | 9/2003 | Mandigo | | 600/300 |
| 6,661,345 B1 * | 12/2003 | Bevan et al. | | 340/575 |
| 6,805,672 B2 * | 10/2004 | Martin et al. | | 600/504 |
| 6,950,027 B2 * | 9/2005 | Banas | | 340/576 |
| 6,968,228 B2 * | 11/2005 | Thornton | | 600/544 |
| 7,113,100 B2 * | 9/2006 | Yoshinori et al. | | 340/575 |
| 7,133,715 B1 * | 11/2006 | Smits et al. | | 600/544 |
| 7,150,715 B2 * | 12/2006 | Collura et al. | | 600/300 |
| 7,222,690 B2 * | 5/2007 | Isaji et al. | | 180/272 |
| 7,253,739 B2 * | 8/2007 | Hammoud et al. | | 340/575 |
| 7,301,465 B2 * | 11/2007 | Tengshe et al. | | 340/575 |
| 7,427,924 B2 * | 9/2008 | Ferrone et al. | | 340/576 |
| 7,440,795 B2 * | 10/2008 | Poezevara | | 600/509 |
| 7,454,243 B2 * | 11/2008 | Silberstein | | 600/544 |
| 7,460,899 B2 * | 12/2008 | Almen | | 600/509 |
| 7,486,987 B2 * | 2/2009 | Kuramori et al. | | 600/546 |
| 7,515,054 B2 * | 4/2009 | Torch | | 340/573.1 |
| 7,639,146 B2 * | 12/2009 | Baura | | 340/573.1 |
| 7,654,948 B2 * | 2/2010 | Kaplan et al. | | 600/26 |
| 7,982,620 B2 * | 7/2011 | Prokhorov et al. | | 340/576 |
| 2002/0095097 A1 * | 7/2002 | Drongelen | | 600/544 |
| 2002/0097160 A1 * | 7/2002 | Oyama | | 340/576 |
| 2002/0105426 A1 * | 8/2002 | Young et al. | | 340/576 |
| 2002/0116352 A1 * | 8/2002 | Kilgard et al. | | 706/25 |
| 2002/0173731 A1 * | 11/2002 | Martin et al. | | 600/549 |
| 2002/0188390 A1 * | 12/2002 | Ichihara et al. | | 701/36 |
| 2003/0060728 A1 * | 3/2003 | Mandigo | | 600/545 |
| 2003/0064748 A1 * | 4/2003 | Stulberger | | 455/556 |
| 2003/0069513 A1 * | 4/2003 | Nesterov et al. | | 600/545 |
| 2003/0125777 A1 * | 7/2003 | Ding et al. | | 607/27 |
| 2004/0044293 A1 * | 3/2004 | Burton | | 600/544 |
| 2004/0077934 A1 * | 4/2004 | Massad | | 600/300 |
| 2005/0075532 A1 * | 4/2005 | Lee et al. | | 600/27 |
| 2005/0283205 A1 * | 12/2005 | Lee et al. | | 607/48 |
| 2006/0116556 A1 * | 6/2006 | Duhamel | | 600/300 |
| 2006/0283652 A1 * | 12/2006 | Yanai et al. | | 180/272 |
| 2007/0032705 A1 * | 2/2007 | Ali | | 600/300 |
| 2007/0066874 A1 * | 3/2007 | Cook | | 600/300 |
| 2007/0112278 A1 * | 5/2007 | Viertio-Oja et al. | | 600/559 |
| 2007/0191688 A1 * | 8/2007 | Lynn | | 600/300 |
| 2008/0221401 A1 * | 9/2008 | Derchak et al. | | 600/301 |
| 2011/0043350 A1 * | 2/2011 | Ben David | | 340/441 |
| 2011/0319721 A1 * | 12/2011 | Hamaguchi | | 600/300 |

FOREIGN PATENT DOCUMENTS

| | | |
|---|---|---|
| JP | H6-038793 | 5/1994 |
| JP | A-2002-165854 | 6/2002 |
| JP | A-2002-334339 | 11/2002 |
| JP | B2-3369201 | 1/2003 |
| JP | A-2004-203281 | 7/2004 |
| JP | A-2004-310034 | 11/2004 |

\* cited by examiner

DETECTOR FOR STATE OF PERSON

TECHNICAL FIELD

The present invention relates to a human condition detecting apparatus for highly accurately detecting a human condition from a vital reaction to a stimulus.

BACKGROUND ART

A variety of devices have been proposed as apparatus for determining a human condition such as an arousal state, a psychological state, or a fatigue state, in order to be used for safety improvement or the like during driving. For example, an arousal determination method is a method of applying a predetermined stimulus to a man, e.g., a driver, letting the man perform a work such as a button operation against the stimulus, and estimating an arousal state, based on a reaction time thereof (e.g., cf. Japanese Patent No. 3369201).

DISCLOSURE OF THE INVENTION

The above-described condition estimation method requires the man subjected to the estimation of the condition, to perform an active work. Therefore, the condition estimation is based on the subjective reaction of the man and high estimation accuracy cannot be expected thereby. If the man is performing a main work (e.g., if a driver of a vehicle is performing a driving operation), the man might not immediately perform the work against the stimulus and the condition could not be accurately estimated. Furthermore, the additional active work except for the main work such as the driving operation will burden the man and the main work might become neglected as the man is preoccupied with the work against the stimulus.

An object of the present invention is therefore to provide a human condition detecting apparatus for highly accurately detecting a human condition, without any burden.

A human condition detecting apparatus according to the present invention is characterized by comprising first stimulus applying means for applying a stimulus for acquisition of reference information to a subject; second stimulus applying means for applying a stimulus for acquisition of condition information to the subject; stimulus reaction detecting means for detecting reactions of the subject to the stimulus applied by the first stimulus applying means and to the stimulus applied by the second stimulus applying means, by an ecological index of the subject; and condition determining means for determining a condition of the subject, based on a comparison between the reaction of the subject to the stimulus applied by the first stimulus applying means and the reaction of the subject to the stimulus applied by the second stimulus applying means.

In this human condition detecting apparatus, the first stimulus applying means applies the stimulus to the subject and the stimulus reaction detecting means detects the reaction of the subject to the stimulus by the physiological index. This reaction of the subject is a physiological response to the stimulus in a normal condition of the subject and reference information as a standard value for determination on the condition. In the human condition detecting apparatus, furthermore, the second stimulus applying means applies the stimulus to the subject and the stimulus reaction detecting means detects the reaction of the subject to the stimulus by the physiological index. This reaction of the subject is a physiological response to the stimulus for detection of the condition of the subject and condition information as an evaluated value for determination on the condition. In the human condition detecting apparatus the condition determining means then makes the comparison between the physiological response to the stimulus applied by the first stimulus applying means and the physiological response to the stimulus applied by the second stimulus applying means and determines the condition of the subject from a change between the physiological responses. Since this human condition detecting apparatus, as described above, uses the objective information of the physiological responses of a man to stimuli (instead of the subjective information of the man) to make the relative comparison between the physiological response (evaluated value) to the stimulus for detection of the condition and the physiological response (reference value) to the stimulus in the normal condition, it is able to highly accurately detect the condition of the man. Since this human condition detecting apparatus is arranged to determine the condition by the physiological responses of the man to the stimuli, it requires no human active work and does not burden the man. Since no burden is required in this manner, while the man is performing the main work such as driving, the detection accuracy of condition does not degrade even during execution of the main work, and the execution of the main work is not neglected during the detection of the condition.

The physiological indices are various indices that can be measured by bioinstrumentation from a man, and include, for example, physiological indices by Electrooculogram (EOG) (blinking and the like), physiological indices by Electroencephalogram (EEG) (an alpha wave, a beta wave, etc.), physiological indices by Electrocardiogram (ECG) (a heart rate and the like), physiological indices by Electro Dermal Activity (EDA) (Skin Potential Response (SPR) and the like), and physiological indices by Electromyogram (EMG). The human condition is, for example, an arousal state, a psychological state (anxiousness, irritation, or the like), or a fatigue state. The stimulus applied by the first stimulus applying means and the stimulus applied by the second stimulus applying means may be stimuli identical with or different from each other, and, when they are the stimuli of the same kind, they may be applied with variation in a parameter such as the intensity or the frequency. The stimulus applied by the second stimulus applying means can be a physical stimulus (e.g., vibration, sound, or light) and may be any other stimulus such as an environment around the subject or a situation of the subject itself (e.g., a full stomach or an empty stomach, and in the case of a vehicle driver, a traffic jam, a travel on an express highway, a travel in the rain, a travel in the midnight, or observation of an accident). Therefore, the second stimulus applying means includes means for generating the physical stimulus and also includes means for applying a stimulus by any one of those environments, situations, and so on.

The foregoing human condition detecting apparatus of the present invention may be arranged so that the stimulus applied by the first stimulus applying means is periodically applied.

In this human condition detecting apparatus, the first stimulus applying means periodically applies the stimulus to the subject and the stimulus reaction detecting means detects reactions of the subject to the stimuli by the physiological index. Since the first stimulus applying means periodically applies the stimulus as described above, the physiological response (reference value) to the stimulus in the human normal condition can be periodically captured. For this reason, even under such circumstances that the human condition varies moment by moment and the physiological response to the stimulus also varies large or small, an accurate reference value can be acquired in the human condition at each moment. As a result, the human condition can be highly accurately detected.

The foregoing human condition detecting apparatus of the present invention may be arranged so that the stimulus applied by the first stimulus applying means is applied before the second stimulus applying means applies the stimulus.

In this human condition detecting apparatus, the first stimulus applying means applies the stimulus to the subject and the stimulus reaction detecting means detects the reaction of the subject to the stimulus by the physiological index. In the human condition detecting apparatus, thereafter, the second stimulus applying means applies the stimulus to the subject and the stimulus reaction detecting means detects the reaction of the subject to the stimulus by the physiological index. Since the first stimulus applying means applies the stimulus before the stimulus for determination on the human condition as described above, the physiological response (reference value) to the stimulus in the human normal condition immediately before the determination on the condition can be acquired at a specific timing. As a consequence, the human condition can be detected more highly accurately. For example, in a case where the human condition is expected to change because of a certain stimulus (e.g., where a man is driving a vehicle and is expected to get on an express highway or get involved in a traffic jam), the first stimulus applying means applies the stimulus before exposure to the stimulus, to acquire the reference value, whereby the human condition upon exposure to the stimulus can be highly accurately detected.

BEST MODE FOR CARRYING OUT THE INVENTION

Embodiments of the human condition detecting apparatus according to the present invention will be described below with reference to the drawings.

The embodiments of the present invention are applications of the human condition detecting apparatus according to the present invention, to condition estimation systems mounted on a vehicle and adapted to estimate an arousal state of a driver. The condition estimation systems according to the present invention are arranged to give a driver a microscopic shaking for reference and a microscopic shaking or environment for estimation of condition and to detect an electro dermal activity (EDA) (especially, a skin potential response (SPR)) as a physiological response to each of the stimuli. The condition estimation systems according to the present invention are arranged then to estimate the arousal state of the driver on the basis of a change between the skin potential response for reference and the skin potential response for estimation of condition and to call driver's attention in case of a low arousal state. The embodiments of the present invention include two forms according to the difference in the timing of generation of the microscopic shaking for reference; the first embodiment is a form of periodically applying the microscopic shaking for reference, and the second embodiment a form of applying the microscopic shaking for reference at a specific timing, e.g., in occurrence of an event (e.g., a traffic jam or an express highway) or a driving situation requiring the condition estimation (e.g., a long-haul travel or a midnight travel).

Figure 1:
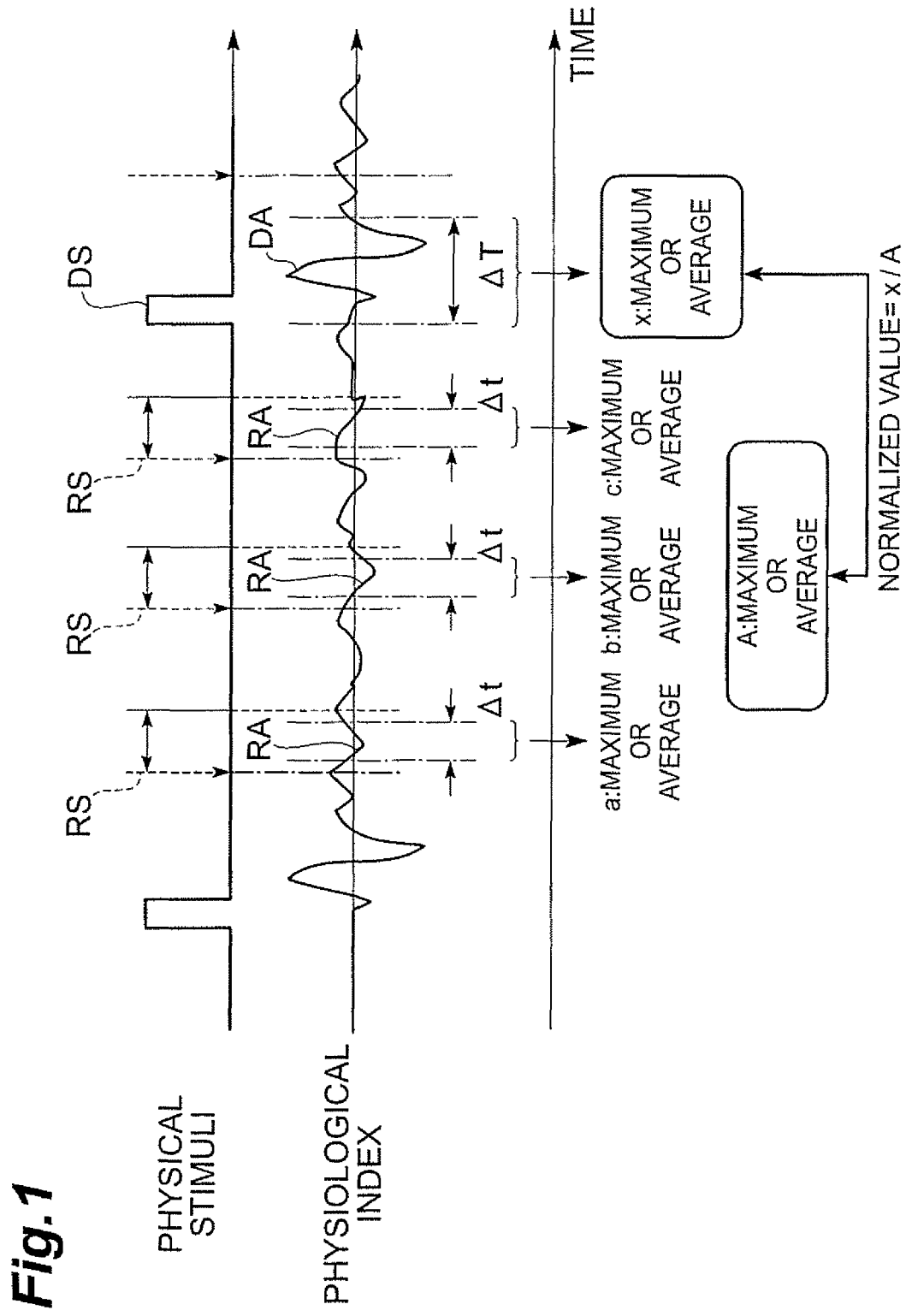
FIG. 1 is a drawing showing an outline of a condition estimation method according to embodiments of the present invention.

Before specific description of the two embodiments, the condition estimation method in the condition estimation systems will be described with reference to FIG. 1. FIG. 1 is a drawing showing an outline of the condition estimation method according to the embodiments of the present invention.

The driver is given microscopic shakings RS, RS, RS as physical stimuli for reference, and electro dermal activities RA, RA, RA as physiological indices against the microscopic shakings RS, RS, RS are detected. Then a maximum or average of change is calculated in a processing section Δt of each electro dermal activity RA. Furthermore, the plurality of maxima or averages are averaged and the resultant average is set as a skin potential response A for reference. This skin potential response A for reference is a physiological response to a physical stimulus in a normal condition of the driver and is a reference value for estimation of the arousal state. The reason why the plurality of physical stimuli for reference (three stimuli in the example of FIG. 1) are given, is that a stable value is obtained as the reference value and even if the physiological indices contain noise, influence of the noise can be suppressed.

Furthermore, the driver is given a microscopic shaking DS as a physical stimulus for estimation of condition and an electro dermal activity DA is detected as a physiological index against the microscopic shaking DS. Then a maximum or average of change is calculated in a processing section ΔT from the electro dermal activity DA and this maximum or average is set as a skin potential response x for estimation of condition. This skin potential response x for estimation of condition is a physiological response to the stimulus applied to the driver and is an evaluated value for estimation of the condition.

The microscopic shakings RS for reference and the microscopic shaking DS for estimation of condition are different in a parameter such as the intensity of vibration, the frequency, or the period of application of vibration, in order to distinguish them from each other. In the example shown in FIG. 1, the microscopic shaking DS for estimation of condition is applied for a longer period of application of vibration. In the second embodiment, the driver can be given as a stimulus in some cases, an environment around the driver such as a traffic jam, or a travel on an express highway, instead of the physical stimulus.

After the skin potential response x for estimation of condition is set, the skin potential response A for reference set immediately before it is made to correspond to the skin potential response x for estimation of condition and the skin potential response x for estimation of condition is divided by the skin potential response A for reference. This relative value of the skin potential response (x/A) is a normalized value resulting from normalization of the skin potential response for estimation of condition on the basis of the skin potential response for reference. Therefore, the relative value of skin potential response (x/A) facilitates estimation of the driver's arousal state on the basis of 1; values around 1 indicate a normal condition, and alertness (degree of arousal) tends to increase with increase of the relative value from 1 and tends to decrease with decrease of the relative value from 1.

The electro dermal activity is a physiological index to electrically measure mental sweating. The reason why the skin potential response is used among the electro dermal activities is that it is generally considered that the skin potential response is a physiological index capable of accurately expressing a change of an arousal state or a psychological state such as anxiousness or irritation and that the time constant of physiological response to change is also small.

In order to evaluate the validity of estimation of the arousal state based on the relative value of skin potential response obtained in this manner, the inventor conducted tests of applying microscopic shakings to various subjects and obtaining the relative values of skin potential responses, and also executed sensory evaluations. Then comparison was made between the relative values of skin potential responses and sensory evaluation values and similar tendencies were observed between arousal states based on the relative values of skin potential responses and arousal states based on the sensory evaluation values, thereby obtaining the good result. The sensory evaluations were obtained by comprehensively assessing the subjective evaluation by forcing the subjects to perform an active task (e.g., a button operation against a stimulus or a response to a question) and the objective evaluation by observing change of face expressions based on images of subject faces.

Figure 2:
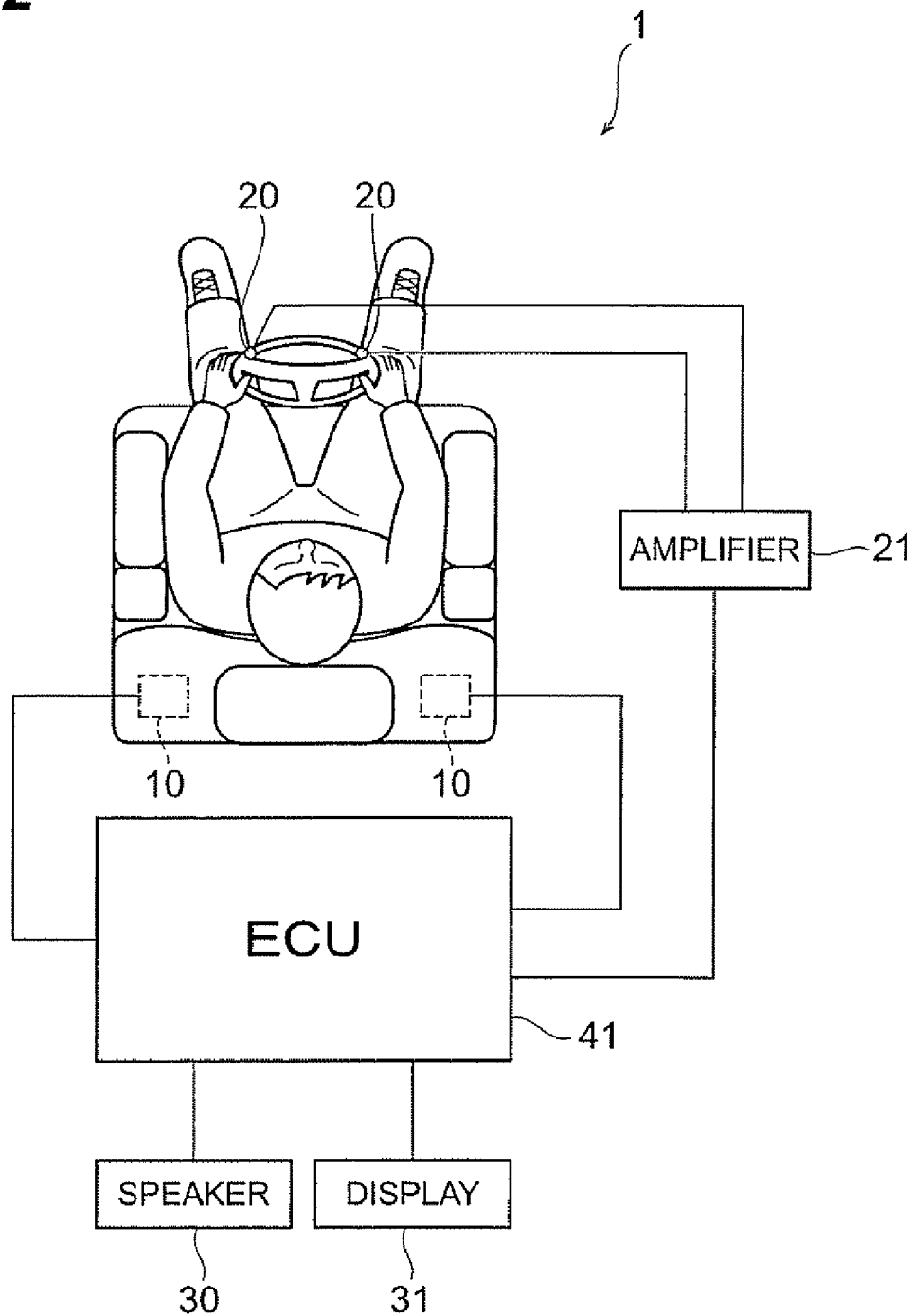
FIG. 2 is a configuration diagram of a condition estimation system according to the first embodiment.
Figure 3:
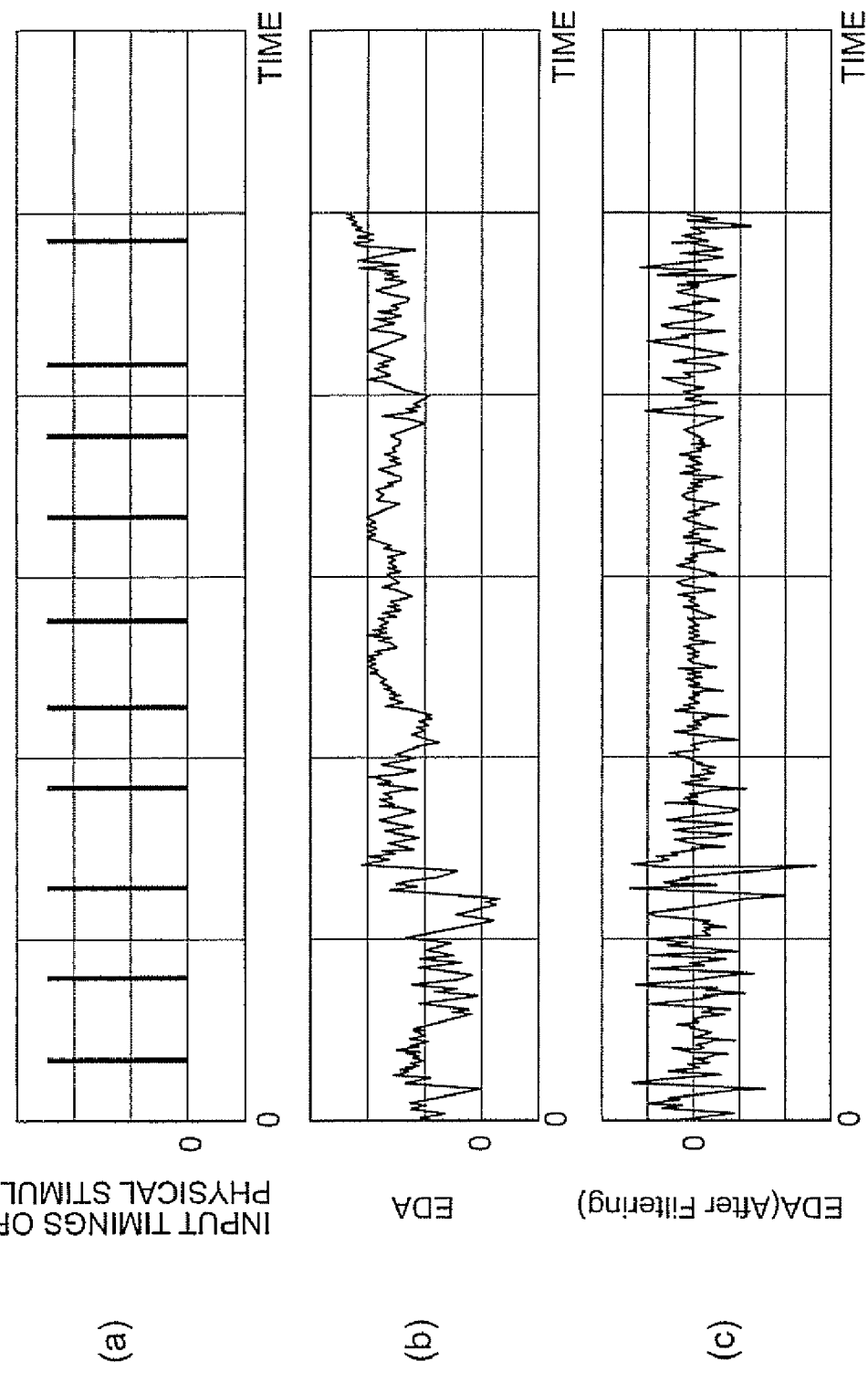
FIG. 3 is an example of a process of condition change according to the first embodiment, wherein (a) is input timings of physical stimuli for estimation of condition, (b) a time change of electro dermal activity (EDA), and (c) a time change after filtering (removal of the DC component) of the electro dermal activity (EDA) shown in (b).
Figure 4:
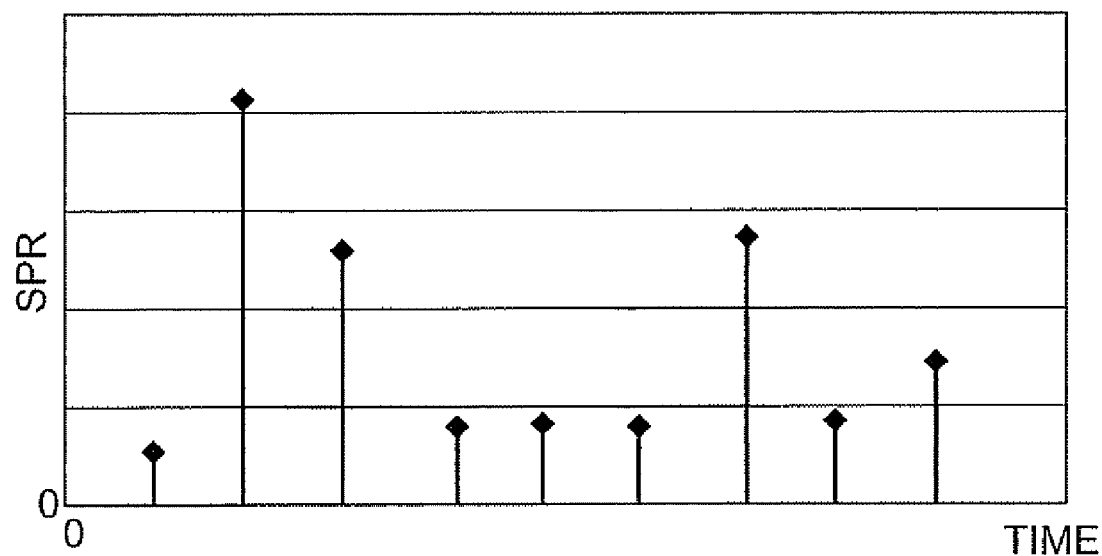
FIG. 4 is an example of time change of skin potential response (SPR) according to the first embodiment.
Figure 5:
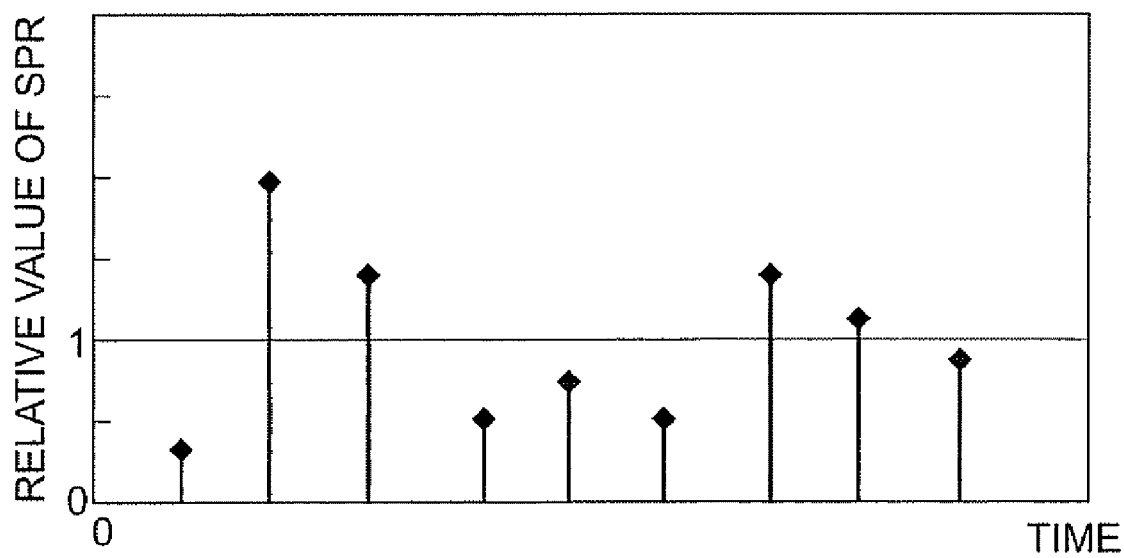
FIG. 5 is an example of time change of relative value of skin potential response (SPR) according to the first embodiment.

The condition estimation system 1 of the first embodiment will be described below with reference to FIGS. 2 to 5. FIG. 2 is a configuration diagram of the condition estimation system according to the first embodiment. FIG. 3 is an example of a process of condition change according to the first embodiment, wherein (a) is input timings of physical stimuli for estimation of condition, (b) a time change of electro dermal activity (EDA), and (c) a time change after filtering (removal of the DC component) of the electro dermal activity (EDA) shown in (b). FIG. 4 is an example of time change of skin potential response (SPR) according to the first embodiment. FIG. 5 is an example of time change of the relative value of skin potential response (SPR) according to the first embodiment.

The condition estimation system 1 is arranged to periodically estimate the driver's arousal state. For implementing it, the condition estimation system 1 periodically applies the microscopic shaking for reference to the driver and periodically acquires the skin potential response for reference. Furthermore, the condition estimation system 1 applies the microscopic shaking for estimation of condition after the application of the microscopic shaking for reference and acquires the skin potential response for estimation of condition. The condition estimation system 1 is provided with shaking generators 10, electro dermal activity sensors 20, an amplifier 21, a speaker 30, a display 31, and an ECU [Electronic Control Unit] 41.

In the first embodiment, the shaking generators 10 correspond to the first stimulus applying means and the second stimulus applying means as set forth in the scope of claims, the electro dermal activity sensors 20 correspond to the stimulus reaction detecting means as set forth in the scope of claims, and the ECU 41 corresponds to the condition determining means as set forth in the scope of claims.

The shaking generators 10 are devices for generating a shaking and apply to the driver the microscopic shaking for reference and the microscopic shaking for estimation of condition, and the shaking for calling driver's attention. The shaking generators 10 are embedded at several locations in a driver's seat. The embedded locations and the number of generators are optional and, for example, a total of six generators are embedded one each on the left side and on the right side of the back, the lower back, and the thighs of the driver. The shaking generators 10 are arranged to permit variation in such parameters as the intensity of generated shakings, the frequency, and the period of generation. When the shaking generators 10 receive a shaking generation signal from the ECU 41, they generate a shaking according to the parameters indicated by the shaking generation signal.

In order to distinguish the shakings generated by the shaking generators 10, from vibrations generated in the vehicle, all the shakings generated by the shaking generators 10 are set at the parameters of the intensity and frequency definitely different from those of the vibrations generated in the vehicle. The microscopic shakings for reference and for estimation of condition are set at the parameter of small intensity, in order to avoid discomfort to the driver. The microscopic shaking for reference and the microscopic shaking for estimation of condition are set at the parameters of different frequencies and different periods of application of shaking, in order to be distinguished from each other. The shaking for calling driver's attention is set at the parameter of large intensity because it is necessary to raise the arousal state of the driver.

The electro dermal activity sensors 20 are sensors for detecting the electro dermal activity (particularly, the Skin Potential Activity (SPA)). The electro dermal activity sensors 20 are mounted one each on the left side and on the right side of the steering wheel where they are kept in contact with the driver's palms, in order to detect the driver's mental sweating. When the electro dermal activity sensors 20 detect the electro dermal activity, they send a detection signal thereof to the amplifier 21. The amplifier 21 amplifies the detection signal and sends the amplified detection signal to the ECU 41. In passing, a man tends to become more likely to cause mental sweating against a stimulus in a high arousal state and tends to become less likely to cause mental sweating in a low arousal state.

The speaker 30 and display 31 are used in common with each system in the vehicle and are used on the occasion of calling driver's attention in the condition estimation system 1. When the speaker 30 receives a sound signal from the ECU 41, it outputs a sound according to the sound signal. When the display 31 receives an image signal from the ECU 41, it displays an image according to the image signal.

The ECU 41 is composed of a CPU [Central Processing Unit], a ROM [Read Only Memory], a RAM [Random Access Memory], and so on, and systematically controls the condition estimation system 1. The ECU 41 periodically transmits a shaking generation signal for generation of the microscopic shaking for reference, and transmits a shaking generation signal for generation of the microscopic shaking for estimation of condition to the shaking generators 10. Then the ECU 41 receives signals amplified from detection signals of the electro dermal activity sensors 20 by the amplifier 21 and estimates the driver's arousal state from the skin potential response for reference and the skin potential response for estimation of condition, based on the signals. Furthermore, when the arousal state is at a level to cause a hindrance to driving, the ECU 41 calls driver's attention by means of the speaker 30, the display 31, and the shaking generators 10.

The ECU 41 transmits the shaking generation signal to indicate the parameters of the microscopic shaking for reference, to the shaking generators 10 at every lapse of a predetermined period. On this occasion, the ECU 41 transmits a prescribed number of shaking generation signals at intervals of a constant time. The predetermined period is a period for periodically acquiring the skin potential response in the driver's normal condition and may be any period of time (e.g., several ten minutes). The constant time is a time a little longer than a time in which the skin potential response can be detected after application of a microscopic shaking for reference. The prescribed number is a number enough to acquire a stable value as the skin potential response to the microscopic shaking in the driver's normal condition, and may be any number (e.g., several times).

The ECU 41 transmits the shaking generation signal to indicate the parameters of the microscopic shaking for estimation of condition, to the shaking generators 10 at a predetermined timing. The predetermined timing may be a timing linked with the generation timing of the microscopic shaking for reference or a timing not linked with the generation timing of the microscopic shaking for reference. FIG. 3(*a*) shows an example of triggers for generation of the microscopic shaking for estimation of condition being input timings of physical stimuli for estimation of the driver's arousal state. The triggers are linked with triggers for generation of the microscopic shaking for reference and the triggers for generation of the microscopic shaking for reference are located immediately before the triggers for estimation of condition.

Every time the ECU 41 generates the microscopic shaking for reference and the microscopic shaking for estimation of condition, it detects the skin potential response to each microscopic shaking, based on the amplified detection signal (electro dermal activity) from the amplifier 21 according to the same method. FIG. 3(*b*) shows an example of time change of the electro dermal activity. First, the ECU 41 filters the electro dermal activity to remove the DC component (skin potential level) from the electro dermal activity. FIG. 3(*c*) shows a time change of the signal after the removal of the DC component from the electro dermal activity of (b) and the electro dermal activity after filtering varies around 0.

Then the ECU 41 extracts a maximum and a minimum from each processing section of the electro dermal activity after the removal of the DC component (a processing section Δt immediately after generation of the microscopic shaking for reference or a processing section ΔT immediately after generation of the microscopic shaking for estimation of condition), and calculates a difference between the maximum and the minimum (absolute maximum; or, a Peak-to-Peak in the processing section). This absolute maximum is a skin potential response to each microscopic shaking. Particularly, in the case for reference, the ECU 41 obtains the prescribed number of skin potential responses for reference, calculates an average thereof, and defines the average as a skin potential response for reference. FIG. 4 shows an example of the skin potential responses detected after generation of the microscopic shakings for estimation of condition.

Every time the ECU 41 detects the skin potential response for estimation of condition, it uses the skin potential response for reference detected immediately before the detection, to divide the skin potential response for estimation of condition by the skin potential response for reference, thereby obtaining the relative value (normalized value) of the skin potential response. When the relative value of skin potential response is around 1, it can be estimated that the driver is in the normal condition. It can also be estimated that as the relative value of skin potential response becomes larger than 1, the driver demonstrates a physiological response greater than in the normal condition and the arousal state tends to be higher. It can also be estimated that as the relative value of skin potential response becomes smaller than 1, the driver demonstrates only a physiological response smaller than in the normal condition, and the alertness tends to be lower. FIG. 5 shows an example of time change of the relative value of skin potential response.

Every time the ECU 41 obtains the relative value of skin potential response, it determines whether the relative value is not more than a threshold. The threshold is a threshold for determining whether the driver is at a level of so low alertness as to affect driving (a level at which driver's attentiveness is lowered), and is set to a value of less than 1. When the ECU 41 determines that the relative value of skin potential response is not more than the threshold, it generates a sound message and image for calling driver's attention, transmits a sound signal consisting of the sound data to the speaker 30, and transmits an image signal consisting of the image data to the display 31. In addition, the ECU 41 sets the shaking generation signal of the parameters for generating a relatively strong shaking enough to raise the driver's arousal state and transmits it to the shaking generators 10. The threshold for determination on the relative value of skin potential response may be set as a single-stage threshold, or multi-stage thresholds may be set so as to stepwise vary the level of calling driver's attention by display, sound, and vibration.

Figure 6:
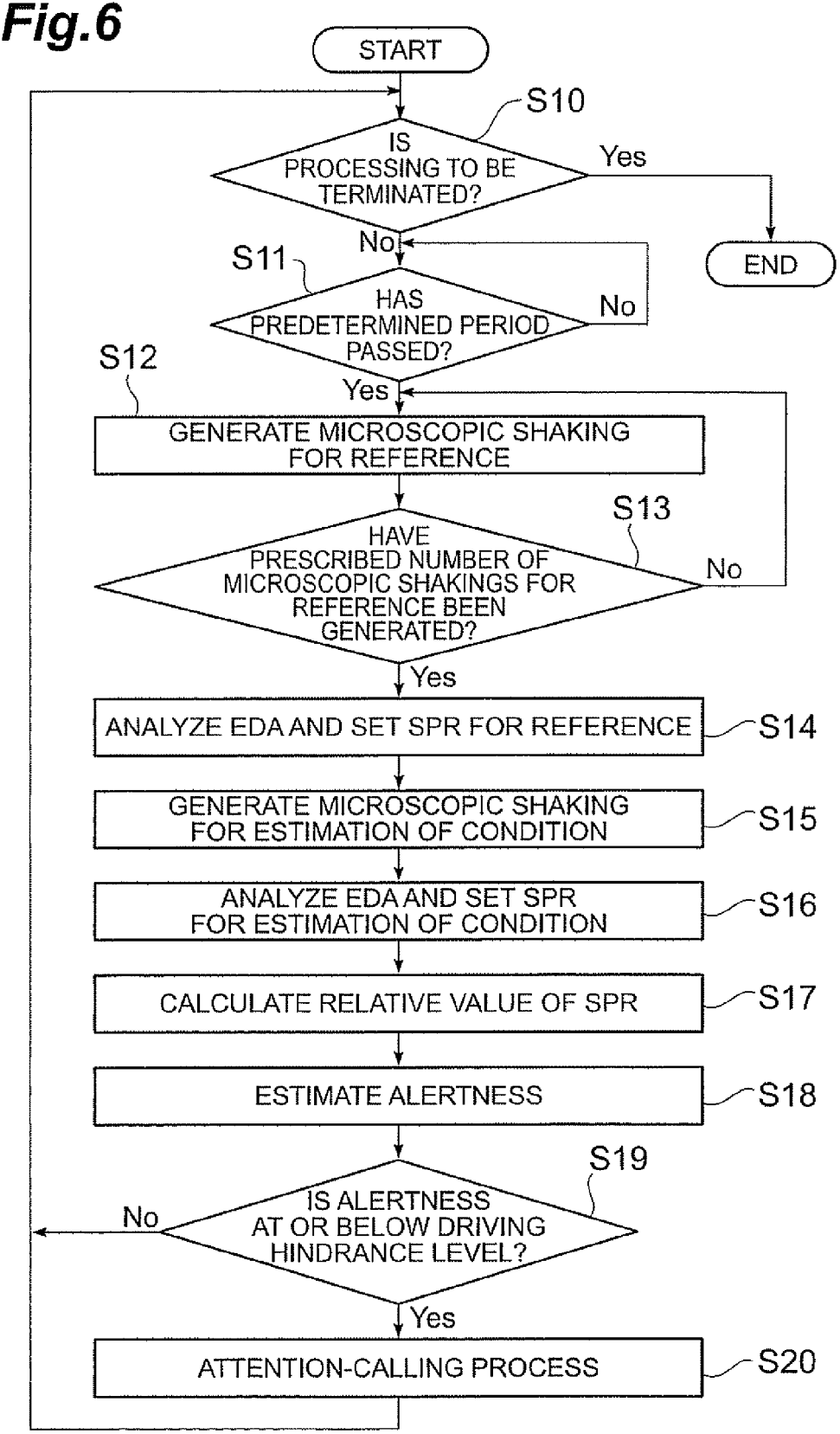
FIG. 6 is a flowchart showing a flow of processing in the condition estimation system of FIG. 2.

The operation of the condition estimation system 1 will be described along the flowchart of FIG. 6, with reference to FIG. 2. The below will describe a case where the microscopic shaking for estimation of condition is also generated after every generation of the microscopic shakings for reference. FIG. 6 is a flowchart showing the flow of processing in the condition estimation system of FIG. 2.

The electro denial activity sensors 20 detect sweating from the driver's palms and transmit their detection signals to the amplifier 21. The amplifier 21 amplifies the detection signals from the electro dermal activity sensors 20 and transmits the amplified detection signals to the ECU 41.

The ECU 41 determines whether the condition estimation processing is to be terminated (S10). When it is determined in S10 that the processing is to be terminated, the ECU 41 terminates the condition estimation processing. The estimation of the arousal state may be carried out throughout the entire duration of driving or only in a predetermined period of driving.

While it is determined in S10 that the processing is not to be terminated, the ECU 41 determines whether the predetermined period has elapsed since generation of the preceding microscopic shaking for reference (S11), and when the predetermined period has not elapsed yet, it waits until the predetermined period has elapsed. When it is determined in S11 that the predetermined period has elapsed, the ECU 41 sets the shaking generation signal for generation of the microscopic shaking for reference and transmits it to the shaking generators 10 (S12). When receiving this shaking generation signal, the shaking generators 10 generate the microscopic shaking for reference (S12). The ECU 41 determines whether the microscopic shaking for reference has been generated the prescribed number of times, upon every lapse of the constant time after the transmission of the shaking generation signal for reference, and when it is not generated the prescribed number of times, the ECU returns to the process of S12 (S13). This causes the driver to periodically sense the microscopic shaking several times from the seat.

Every time the ECU 41 generates the microscopic shaking for reference, it analyzes the electro dermal activity immediately after generation of the microscopic shaking for reference on the basis of the amplified detection signal from the amplifier 21 and detects the skin potential response to the microscopic shaking for reference (S14). Then the ECU 41 averages the skin potential responses to the prescribed number of microscopic shakings for reference and sets the average as a skin potential response for reference at this time (S14). This results in periodically obtaining the skin potential response to the microscopic shaking in the driver's normal condition.

Subsequently, the ECU 41 sets the shaking generation signal for generation of the microscopic shaking for estimation of condition and transmits it to the shaking generators 10 (S15). When receiving this shaking generation signal, the shaking generators 10 generate the microscopic shaking for estimation of condition (S15). This causes the driver to periodically sense one microscopic shaking from the seat.

Every time the ECU 41 generates the microscopic shaking for estimation of condition, it analyzes the electro dermal signal immediately after the generation of the microscopic shaking for estimation of condition on the basis of the amplified detection signal from the amplifier 21 and sets the skin potential response to the microscopic shaking for estimation of condition (S16). This results in obtaining the skin potential response to the microscopic shaking for determination on the driver's arousal state.

After obtaining the skin potential response for estimation of condition, the ECU 41 divides this skin potential response for estimation of condition by the skin potential response for reference immediately before it, to calculate the relative value of skin potential response (S17). This results in obtaining an index for determination on the driver's arousal state, based on the latest skin potential response in the driver's normal condition.

Then the ECU 41 estimates the alertness of the driver on the basis of this relative value of skin potential response (S18) and determines whether the driver's condition is at or below the level to cause a hindrance to driving (specifically, whether the relative value of skin potential response is not more than the threshold) (S19). When it is determined in S19 that the driver's condition is above the level to cause a hindrance to driving, the ECU 41 returns to the process of S10.

When it is determined in S19 that the driver's condition is at or below the level to cause a hindrance to driving, the ECU 41 generates the sound message and image of guidance for calling driver's attention, transmits the sound signal to the speaker 30, and transmits the image signal to the display 31 (S20). When receiving this sound signal, the speaker 30 outputs an attention-calling message according to the sound signal (S20). When receiving the image signal, the display 31 displays an attention-calling image according to the image signal (S20). Furthermore, the ECU 41 generates the shaking generation signal for raising the driver's alertness and transmits the shaking generation signal to the shaking generators 10 (S20). When receiving this shaking generation signal, the shaking generators 10 generate a strong shaking. These sound, display, and shaking raise the driver's alertness to increase attentiveness for driving.

Since this condition estimation system 1 is arranged to apply the stimuli inoffensive to the driver and to estimate the condition from a change of the skin potential response to the stimuli, it is able to highly accurately estimate the driver's arousal state on the basis of the objective information, without burdening the driver (i.e., without need for the driver to perform any active task). The driver is prevented from neglecting the driving itself because of the condition estimation and attention is called with reduction in the arousal state. This enhances the safety.

Particularly, the condition estimation system 1 is arranged to apply the microscopic shaking in every predetermined period to the driver, whereby the skin potential response to the microscopic shaking in the driver's normal condition can be periodically captured. For this reason, the condition estimation system uses the latest skin potential response (reference value) to the microscopic shaking in the driver's normal condition in the estimation of the driver's arousal state, whereby the driver's arousal state can be highly accurately estimated. The driver's condition varies moment by moment, and the driver sometimes demonstrates a large physiological response or sometimes demonstrates a small physiological response to the microscopic shaking. Therefore, the use of the latest reference value in the determination on the condition permits the driver's arousal state to be accurately estimated.

Figure 7:
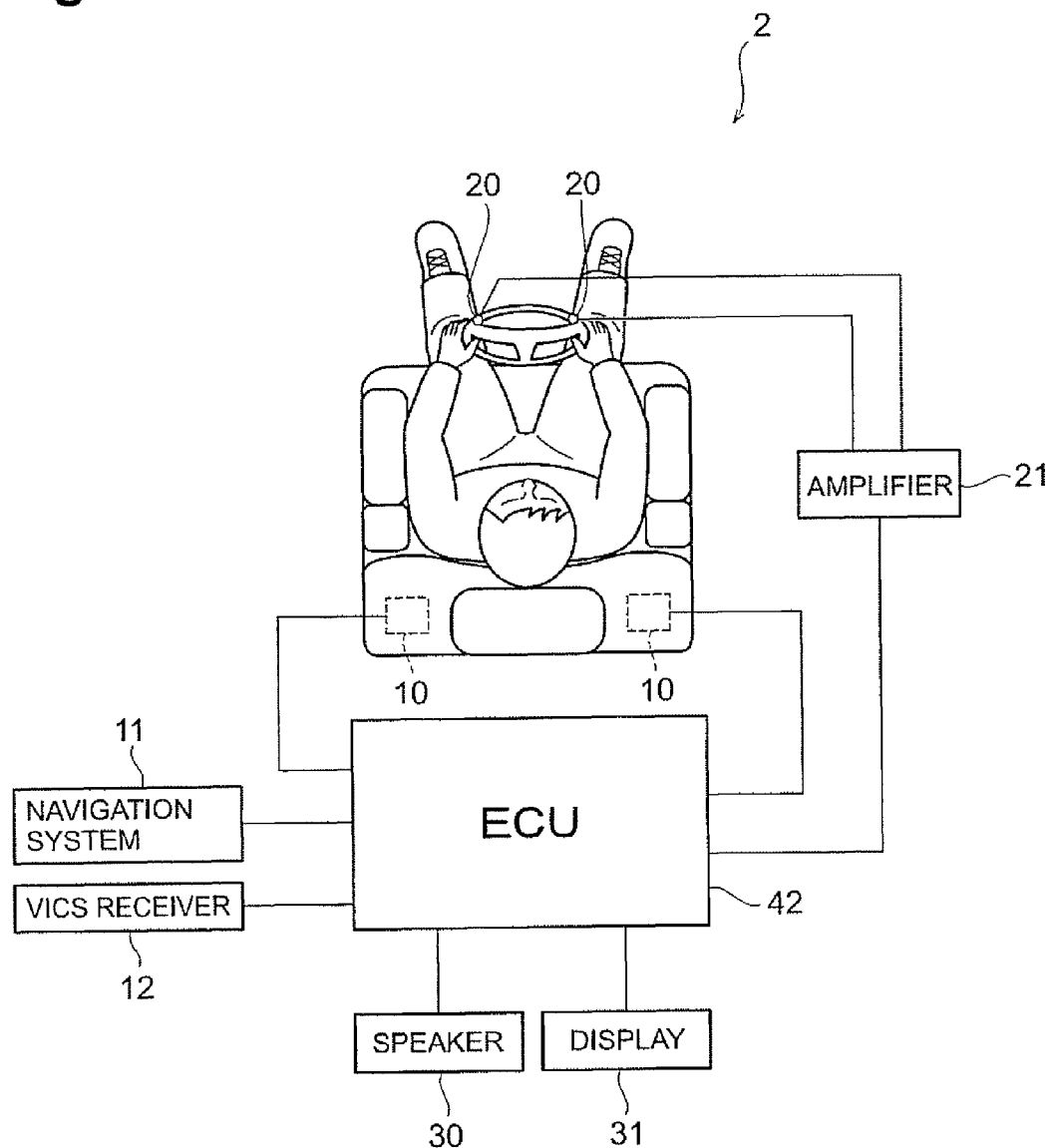
FIG. 7 is a configuration diagram of a condition estimation system according to the second embodiment.

The condition estimation system 2 according to the second embodiment will be described with reference to FIG. 7. FIG. 7 is a configuration diagram of the condition estimation system according to the second embodiment. The same reference symbols will be used to denote the same configuration in the condition estimation system 2 as in the condition estimation system 1 of the first embodiment, without redundant description.

The condition estimation system 2 is arranged to estimate the driver's arousal state only when it is necessary to estimate the driver's condition. For implementing it, every time an event is expected to occur, the condition estimation system 2 applies the microscopic shaking for reference before occurrence of the event and acquires the skin potential response for reference. Furthermore, when an event occurs, the condition estimation system 2 acquires the skin potential response for estimation of condition during occurrence of the event. This event is an environment in which the driver is put during driving and is, for example, a travel in a traffic jam or on an express highway. The condition estimation system 2 applies the microscopic shaking for reference in a situation requiring the estimation of condition and acquires the skin potential response for reference. Furthermore, the condition estimation system 2 applies the microscopic shaking for estimation of condition after acquisition of the skin potential response for reference and acquires the skin potential response for estimation of condition. This situation requiring the estimation of condition is a driver's driving situation and is, for example, a long-time passage after a start of driving, or midnight driving. The condition estimation system 2 is provided with the shaking generators 10, a navigation system 11, a VICS [Vehicle Information and Communication System] receiver 12, the electro dermal activity sensors 20, the amplifier 21, the speaker 30, the display 31, and an ECU 42.

In the second embodiment, the shaking generators 10 correspond to the first stimulus applying means and the second stimulus applying means as set forth in the scope of claims, the environment itself in which the driver is put during driving also corresponds to the second stimulus applying means as set forth in the scope of claims, the electro dermal activity sensors 20 correspond to the stimulus reaction detecting means as set forth in the scope of claims, and the ECU 42 corresponds to the condition determining means as set forth in the scope of claims.

The navigation system 11 detects a current location and progress of the host vehicle, searches for a route to a set destination, and provides guidance by voice and display so as to implement traveling along the route. The navigation system 11 transmits a navigation signal containing currently traveling road information, route information to the destination, etc. to the ECU 42. The VICS receiver 12 receives a VICS signal from a beacon unit installed on a road or a VICS signal given by FM multiplex broadcasting, demodulates the VICS signal, and transmits the demodulated VICS signal to the ECU 42. In a case where the navigation system 11 is adapted to receive the VICS the navigation system 11 may acquire the VICS information and in that case the VICS receiver 12 does not have to be installed.

The ECU 42 is composed of a CPU, a ROM, a RAM, and so on, and systematically controls the condition estimation system 2. The ECU 42 receives the navigation signal from the navigation system 11 and the VICS signal from the VICS receiver 12 and on the occasion of occurrence of an event (a traffic jam or the like), it transmits the shaking generation signal for generation of the microscopic shaking for reference to the shaking generators 10 before occurrence of the event. When the driving situation is a situation requiring the estimation of condition (e.g., a long-haul travel or the like), the ECU 42 transmits the shaking generation signal for generation of the microscopic shaking for reference to the shaking generators 10 and transmits the shaking generation signal for generation of the microscopic shaking for estimation of condition to the shaking generators 10 thereafter. Then the ECU 42 receives signals amplified for the detection signals of the electro dermal activity sensors 20 by the amplifier 21 and estimates the driver's arousal state from the skin potential response for reference and the skin potential response for estimation of condition on the basis of the signals. Furthermore, when the arousal state is at or below the level to cause a hindrance to driving, the ECU 42 calls driver's attention by means of the speaker 30, the display 31, and the shaking generators 10.

First, a processing procedure of event treatment will be described. The ECU 42 determines whether an event will occur within a predetermined time, based on the route information and the road information by the navigation signal and on traffic jam information by the VICS signal. The event is a driving environment in which the driver's arousal state can degrade and is, for example, a situation of getting on an express highway or a situation of being stuck in a traffic jam. The predetermined time is a time a little longer than a time enough to apply the microscopic shaking for reference a prescribed number of times and to detect the skin potential responses for reference. When the ECU 42 determines that an event will occur within the predetermined time, it transmits the prescribed number of shaking generation signals to indicate the parameters of the microscopic shaking for reference, to the shaking generators 10, as in the case of the first embodiment.

After generation of the microscopic shaking for reference and during occurrence of the event, the ECU 42 detects each of the skin potential response for reference and the skin potential response for estimation of condition by a method similar to that in the first embodiment. Since the skin potential response during occurrence of the event is detected as the skin potential response for detection of the condition, the ECU 42 determines whether the current situation is in occurrence of the event, based on the navigation signal and the VICS signal, and detects the skin potential response for estimation of condition from the electro dermal activity during occurrence of the event.

Next, a processing procedure of driving situation treatment will be described. The ECU 42 determines whether the current driving situation is a situation requiring the estimation of condition, from a lapse of time from a start of driving, the time in driving, or the like. The situation requiring the estimation of condition is a driving situation in which the driver's arousal state is expected to become lowered, and is, for example, a case where several hours have elapsed since a start of driving (long-haul driving), a case of driving during the period from the midnight to early morning (midnight driving), or a case where driving is started around the noon or around 7 pm (driving after a meal). When the ECU 42 determines that the current situation is a situation requiring the estimation of condition, it transmits the prescribed number of shaking generation signals to indicate the parameters of the microscopic shaking for reference, to the shaking generators 10, as in the first embodiment. Furthermore, after the generation of the microscopic shakings for reference, the ECU 42 transmits the shaking generation signal to indicate the parameters of the microscopic shaking for estimation of condition, to the shaking generators 10, as in the first embodiment.

When the microscopic shaking for reference is generated and when the microscopic shaking for estimation of condition is generated, the ECU 42 detects each of the skin potential response for reference and the skin potential response for estimation of condition by a method similar to that in the first embodiment.

When the ECU 42 detects the skin potential response for estimation of condition, it uses the skin potential response for reference and the skin potential response for estimation of condition detected, to obtain the relative value of skin potential response by a method similar to that in the first embodiment. Then the ECU 42 makes the determination between the relative value of skin potential response and the threshold, as in the first embodiment, and when the relative value of skin potential response is determined to be not more than the threshold, the ECU 42 transmits each of the signals for calling driver's attention.

Figure 8:
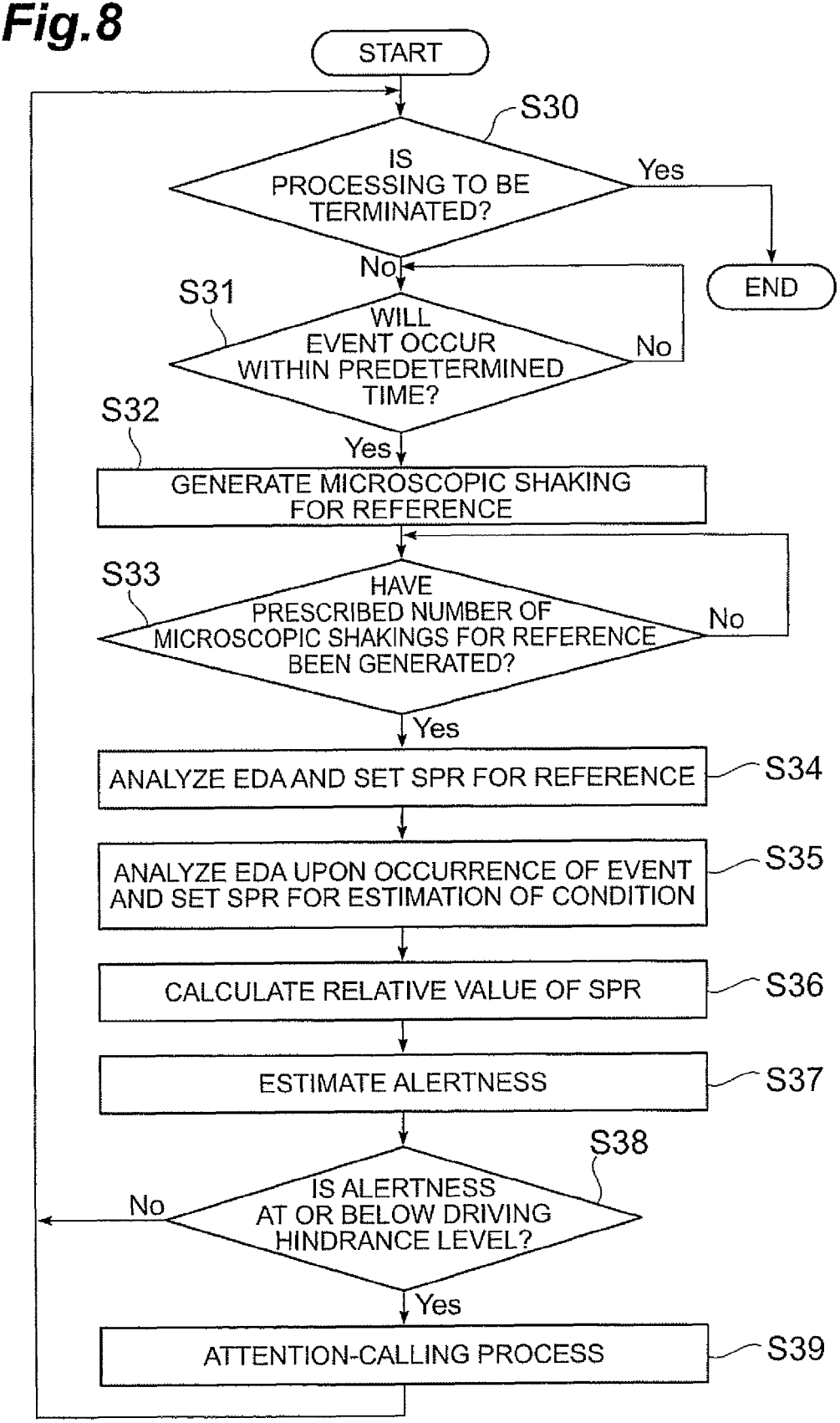
FIG. 8 is a flowchart showing a flow of processing of event treatment in the condition estimation system of FIG. 7.
Figure 9:
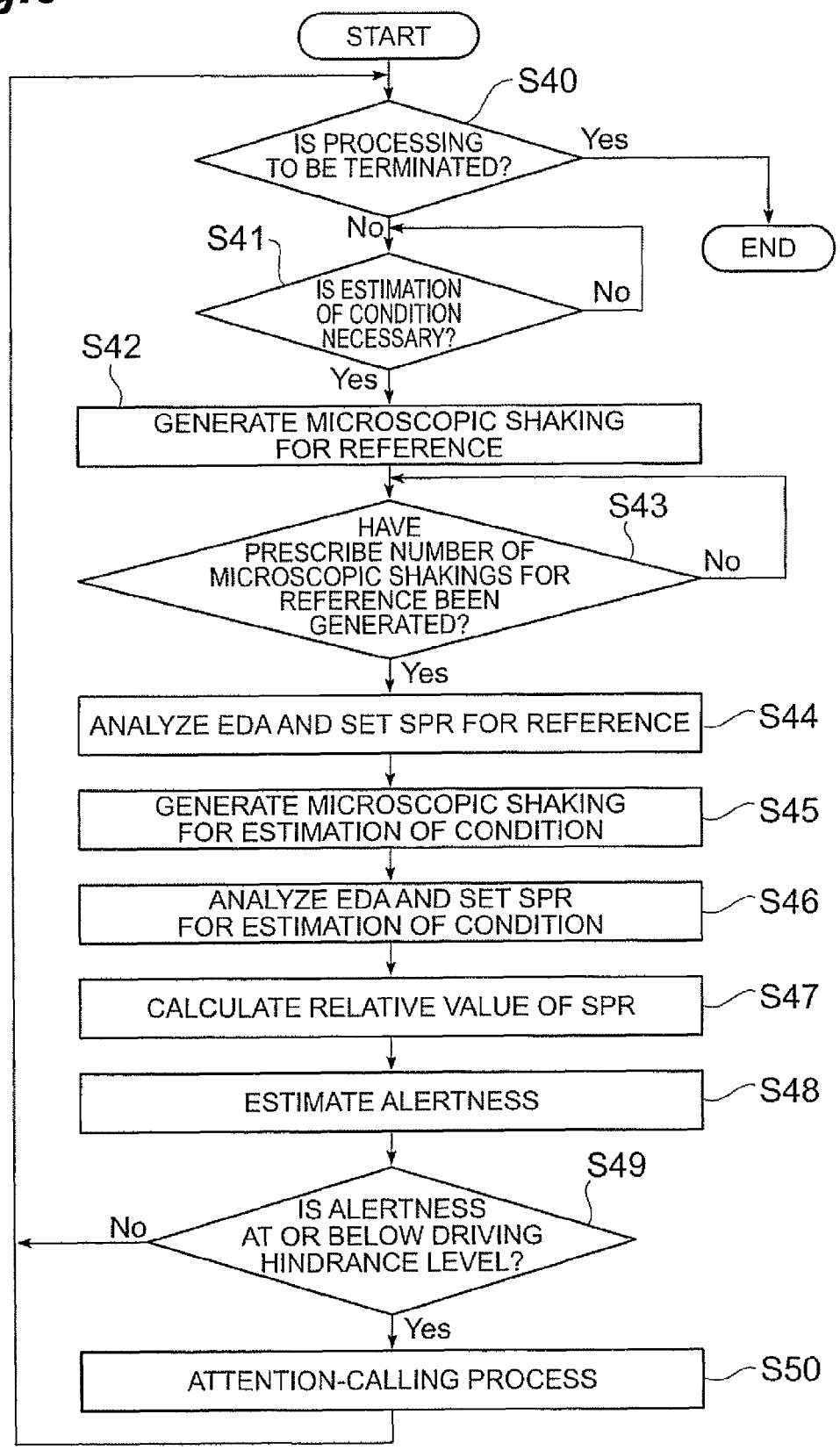
FIG. 9 is a flowchart showing a flow of processing of driving situation treatment in the condition estimation system of FIG. 7.

The operation of the condition estimation system 2 will be described with reference to FIG. 7. The operation of event occurrence treatment will be first described along the flowchart of FIG. 8 and then the operation of driving situation treatment will be described along the flowchart of FIG. 9. FIG. 8 is the flowchart showing the flow of the processing of event treatment in the condition estimation system of FIG. 7. FIG. 9 is the flowchart showing the flow of the processing of driving situation treatment in the condition estimation system of FIG. 7.

In the same manner as in the first embodiment, the electro dermal activity sensors 20 detect sweating from the driver's palms, the amplifier 21 amplifies the detection signals thereof, and the amplified detection signals are transmitted to the ECU 42. The navigation system 11 performs the detection of the current location, the route guidance, etc. and transmits the navigation signal containing the road information, the route information, etc. to the ECU 42. The VICS receiver 12 receives the VICS signal and transmits the demodulated VICS signal to the ECU 42.

First, the processing of event treatment will be described. The ECU 42 determines whether the condition estimation processing is to be terminated (S30). When it is determined in S30 that the processing is to be terminated, the ECU 42 terminates the condition estimation processing.

While it is determined in S30 that the processing is not to be terminated, the ECU 42 determines whether an event will occur within the predetermined time, based on the navigation signal and the VICS signal (S31) and, when no event will occur within the predetermined time, it waits until an event occurs. When it is determined in S31 that an event will occur within the predetermined time, the ECU 42 transmits the prescribed number of shaking generation signals for reference, to the shaking generators 10 by the same processes as S12 and S13 in the first embodiment (S32, S33). Then the shaking generators 10 generate the prescribed number of microscopic shakings for reference (S32). This causes the driver to sense some microscopic shakings from the seat, before occurrence of the event.

After the generation of the microscopic shakings for reference, the ECU 42 analyzes the electro dermal signals by the same process as S14 in the first embodiment, and sets the skin potential response for reference (S34). This results in obtaining the skin potential response to the microscopic shaking in the driver's normal condition, immediately before the event.

The ECU 42 determines whether the event has occurred, based on the navigation signal and the VICS signal. When it is determined that the event has occurred, the ECU 42 analyzes the electro dermal signal by the same process as S16 in the first embodiment, to set the skin potential response for estimation of condition (S35). This results in obtaining the driver's skin potential response during occurrence of the event.

After the skin potential response for estimation of condition is acquired, the ECU 42 divides the skin potential response for estimation of condition during occurrence of the event by the skin potential response for reference immediately before occurrence of the event, to calculate the relative value of skin potential response (S36). This results in obtaining an index for determining the driver's arousal state during occurrence of the event, based on the skin potential response in the driver's normal condition acquired immediately before the event.

Since the respective operations in S37-S39 are the same operations as those in S18-S20 in the first embodiment, the description thereof is omitted herein.

Next, the processing of driving situation treatment will be described. The ECU 42 determines whether the condition estimation processing is to be terminated (S40). When it is determined in S40 that the processing is to be terminated, the ECU 42 terminates the condition estimation processing.

While it is determined in S40 that the processing is not to be terminated, the ECU 42 determines whether the current driving situation is a situation requiring the estimation of condition (S41) and, when the current situation is not one requiring the estimation of condition, the ECU 42 waits until such a driving situation. When it is determined in S41 that the current driving situation is a situation requiring the estimation of condition, the ECU 42 transmits the prescribed number of shaking generation signals for reference, to the shaking generators 10 by the same processes as S12 and S13 in the first embodiment (S42, S43). Then the shaking generators 10 generate the prescribed number of microscopic shakings for reference (S42). This causes the driver to sense several microscopic shakings from the seat, under a driving situation in which the arousal state can degrade.

After the generation of the microscopic shakings for reference, the ECU 42 analyzes the electro dermal signals by the same process as S14 in the first embodiment and sets the skin potential response for reference (S44). This results in obtaining the skin potential response as a reference under the driving situation in which the arousal state can degrade.

After the setting of the skin potential response for reference, the ECU 42 transmits the shaking generation signal for estimation of condition to the shaking generators 10 by the same process as S15 in the first embodiment (S45). Then the shaking generators 10 generate the microscopic shaking for estimation of condition (S45). This causes the driver to sense one microscopic shaking from the seat.

After the generation of the microscopic shaking for estimation of condition, the ECU 42 analyzes the electro dermal signal by the same process as S16 in the first embodiment and sets the skin potential response for estimation of condition (S46). This results in obtaining the skin potential response for determining the driver's arousal state under the driving situation in which the arousal state can degrade.

After acquisition of the skin potential response for estimation of condition, the ECU 42 divides the skin potential response for estimation of condition in the driving situation requiring the estimation of the condition, by the skin potential response for reference, to calculate the relative value of skin potential response (S47). This results in obtaining an index for determining the driver's arousal state under the driving situation in which the arousal state can degrade.

Since the respective operations in S48-S50 are the same as those in S18-S20 in the first embodiment, the description thereof is omitted herein.

This condition estimation system 2 is able to highly accurately estimate the driver's arousal state on the basis of the objective information, without burdening the driver, as in the first embodiment. Particularly, since the condition estimation system 2 is arranged to apply the microscopic shakings for reference at the specific timing based on the event or the driving situation, it is able to capture the skin potential response as a reference at the specific timing. For this reason, it is able to highly accurately estimate the driver's arousal state at any time in an environment or a driving situation in which it is desirable to estimate the driver's condition.

The above described the embodiments of the present invention, and it should be noted that the present invention can be carried out in various forms without having to be limited to the above embodiments.

For example, the embodiments were the applications to the apparatus mounted on the vehicle and arranged to estimate the alertness (arousal state) as a condition of the driver of the vehicle, but the present invention can also be applied to estimation of conditions of various people such as drivers of other vehicles, guards of various plants, and night workers, or to apparatus for estimating other conditions than the arousal state, e.g., psychological states (anxiousness, irritation, and boredom), or a fatigue state.

The embodiments used the shakings generated from the seat, as the physical stimuli applied to a man, but it is also possible to use a variety of physical stimuli; for example, the other physical stimuli such as sounds or light may be generated, or it is also possible to use vibration, light, or sound steadily emitted from equipment.

The embodiments adopted the configuration in which the system side applied the both physical stimuli for reference and for estimation of condition as the same physical stimuli by the microscopic shakings from the seat (which were the same physical stimuli but were different in the parameters of the period of application of vibration, the strength of vibration, the period of vibration, etc. between for the reference and for the estimation of condition), but it is also possible to adopt a configuration in which different physical stimuli are applied.

The embodiments used the electro dermal activity (EDA), particularly, the skin potential response (SPR) as a physiological index, but it is also possible to use a variety of physiological indices; for example, it is also possible to use the physiological indices such as the physiological indices by electrooculogram (EOG) (blinking and the like), the physiological indices by electroencephalogram (EEG) (an alpha wave, a beta wave, etc.), the physiological indices by electrocardiogram (ECG) (a heart rate and the like), the physiological indices by electromyogram (EMG), and so on, and it is also possible to use the other physiological indices such as a skin resistance level (SRL), a skin resistance response (SRR), and a skin potential level (SPL) among the electro dermal activities. Furthermore, the condition does not always have to be estimated from only one physiological index, but the condition may be estimated by a combination of two or more physiological indices.

The embodiments adopted the configuration wherein driver's attention was called by the image display, the sound output, the vibration, or the like when the arousal state became below the level to cause a hindrance to driving, but it is also possible to adopt a configuration wherein attention is called by any other means such as an alarm buzzer, or the vehicle may be arranged to control driving so as to enhance the safety by changing the control timing or control threshold of a driving support system (e.g., a pre-crash safety system, an adaptive cruise control system, or a lane keep system) when the condition becomes not more than the level to cause a hindrance to driving. It is also possible to adopt a configuration wherein a human condition is detected and the human condition thus detected is outputted.

The second embodiment adopted the configuration wherein the navigation system and the VICS were used to detect the event in which the driving environment was expected to change, but it is also possible to adopt a configuration wherein the event is detected by any other means such as reception of traffic information by the radio.

INDUSTRIAL APPLICABILITY

The present invention is able to highly accurately detect the human condition, without burdening a man.

The invention claimed is:

1. A human condition detecting apparatus comprising:
   first stimulus applying means for applying a first stimulus for acquisition of reference information to a driver;
   second stimulus applying means for applying a second stimulus for acquisition of condition information to the driver;
   stimulus reaction detecting means for detecting reactions of the driver to the first stimulus applied by the first stimulus applying means as a reference information by an electro dermal activity of the driver and for detecting reactions of the driver to the second stimulus applied by the second stimulus applying means as a condition information by the electro dermal activity of the driver;
   an event determining means for determining whether a traffic-related event will occur within a predetermined time, the first stimulus applying means applying the first stimulus for acquisition of the reference information to the driver immediately prior to the traffic-related event, and the second stimulus applying means applying the second stimulus for acquisition of the condition information to the driver during the traffic-related event; and
   condition determining means for determining a condition of the driver, based on a comparison between the reference information and the condition information, wherein
      the first stimulus applied by the first stimulus applying means is applied multiple times at a predetermined interval and one reference information is obtained from the reactions of the driver to the first stimulus applied multiple times, and
      the first stimulus applying means applies the first stimulus prior to the traffic-related event every time the event determining means determines that the traffic-related event will occur.

2. The human condition detecting apparatus according to claim 1, wherein the reference information is periodically obtained at every lapse of a predetermined period.

3. The human condition detecting apparatus according to claim 1, wherein the first stimulus applied by the first stimulus applying means is applied before the second stimulus applying means applies the second stimulus.

4. The human condition detecting apparatus according to claim 1, wherein the stimulus reaction detection means is mounted on a steering wheel.

5. The human condition detecting apparatus according to claim 1, wherein the second stimulus applied by the second stimulus applying means is applied for a longer time period than the first stimulus applied by the first stimulus applying means.

6. A human condition detecting method comprising:
   applying a first stimulus for acquisition of reference information to a driver;
   applying a second stimulus for acquisition of condition information to the driver;
   detecting reactions of the driver to the first stimulus applied for acquisition of reference information as a reference information by an electro dermal activity of the driver and for detecting reactions of the driver to the second stimulus applied for acquisition of condition information as a condition information by the electro dermal activity of the driver;
   determining whether a traffic-related event will occur within a predetermined time, and applying the first stimulus for acquisition of the reference information to the driver immediately prior to the traffic-related event and applying the second stimulus for acquisition of the condition information to the driver being applied during the traffic-related event;
   determining a condition of the driver based on a comparison between the reference information and the condition information, wherein
      the first stimulus for acquisition of the reference information is applied multiple times at a predetermined interval and one reference information is obtained from the reactions of the driver to the first stimulus applied multiple times, and
      the first stimulus for acquisition of the reference information to a driver is applied immediately prior to the traffic-related event every time the step of determining whether the traffic-related event will occur determines that the traffic-related event will occur.

7. The human condition detecting method according to claim 6, wherein the reference information is periodically obtained at every lapse of a predetermined period.

8. The human condition detecting method according to claim 6, wherein the first stimulus applied for acquisition of reference information is applied before applying the second stimulus for acquisition of condition information.

* * * * *